United States Patent [19]
Yoon

[11] Patent Number: 5,584,849
[45] Date of Patent: *Dec. 17, 1996

[54] RETRACTABLE SAFETY PENETRATING INSTRUMENT WITH SAFETY SHIELD AND MULTIPLE TRIGGERING AND/OR MOVING COMPONENTS

[76] Inventor: InBae Yoon, 2101 Highland Ridge Dr., Phoenix, Md. 21131

[ * ] Notice: The term of this patent shall not extend beyond the expiration date of Pat. No. 5,431,635.

[21] Appl. No.: 374,375

[22] Filed: Jan. 18, 1995

Related U.S. Application Data

[63] Continuation-in-part of Ser. No. 247,205, May 20, 1994, and a continuation-in-part of Ser. No. 254,007, Aug. 10, 1994, Pat. No. 5,478,317, said Ser. No. 247,205, May 20, 1994, is a division of Ser. No. 800,507, Nov. 27, 1991, abandoned, said Ser. No. 254,007, Jun. 3, 1994, Pat. No. 5,478,317, and a continuation of Ser. No. 800,507, Nov. 27, 1991, abandoned.

[51] Int. Cl.$^6$ ................................................ A61M 5/70
[52] U.S. Cl. ........................... 606/185; 604/165; 604/170
[58] Field of Search .................................. 128/751, 752, 128/753, 754; 604/95, 158, 159, 162, 163, 164, 165, 170, 272, 274, 280, 169; 606/167, 171, 185

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,802,275 | 4/1989 | Haber et al. . |
| 4,817,603 | 4/1989 | Turner et al. . |
| 4,869,717 | 9/1989 | Adair . |
| 4,889,117 | 12/1989 | Stevens . |
| 4,900,307 | 2/1990 | Kulli . |

(List continued on next page.)

FOREIGN PATENT DOCUMENTS

| | | |
|---|---|---|
| 2544262 | 4/1977 | Germany . |
| 1435246 | 11/1988 | U.S.S.R. . |

*Primary Examiner*—Guy V. Tucker

[57] ABSTRACT

A safety penetrating instrument for establishing a portal in the wall of an anatomical cavity includes a housing, a portal sleeve either fixed or distally-biased relative to the housing, a penetrating member disposed within the portal sleeve, a distally-biased safety shield disposed between the portal sleeve and the penetrating member, a retracting mechanism for moving the penetrating member proximally from a penetrating member extended position to a penetrating member retracted position, a locking mechanism for locking the penetrating member in the penetrating member extended position, and a releasing mechanism responsive to penetration of the safety penetrating instrument into the anatomical cavity for triggering release of the locking mechanism to permit the retracting mechanism to move the penetrating member proximally to the penetrating member retracted position. The locking mechanism can either prevent proximal movement of the penetrating member during penetration or permit a predetermined amount of proximal movement of the penetrating member during penetration of the anatomical cavity wall, in which case a penetrating member bias mechanism can be provided for biasing the penetrating member distally in the locked penetrating member extended position.

29 Claims, 9 Drawing Sheets

U.S. PATENT DOCUMENTS

| | | |
|---|---|---|
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 9/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,226,426 | 7/1993 | Yoon . |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |
| 5,431,635 | 7/1995 | Yoon ........................................ 604/165 |

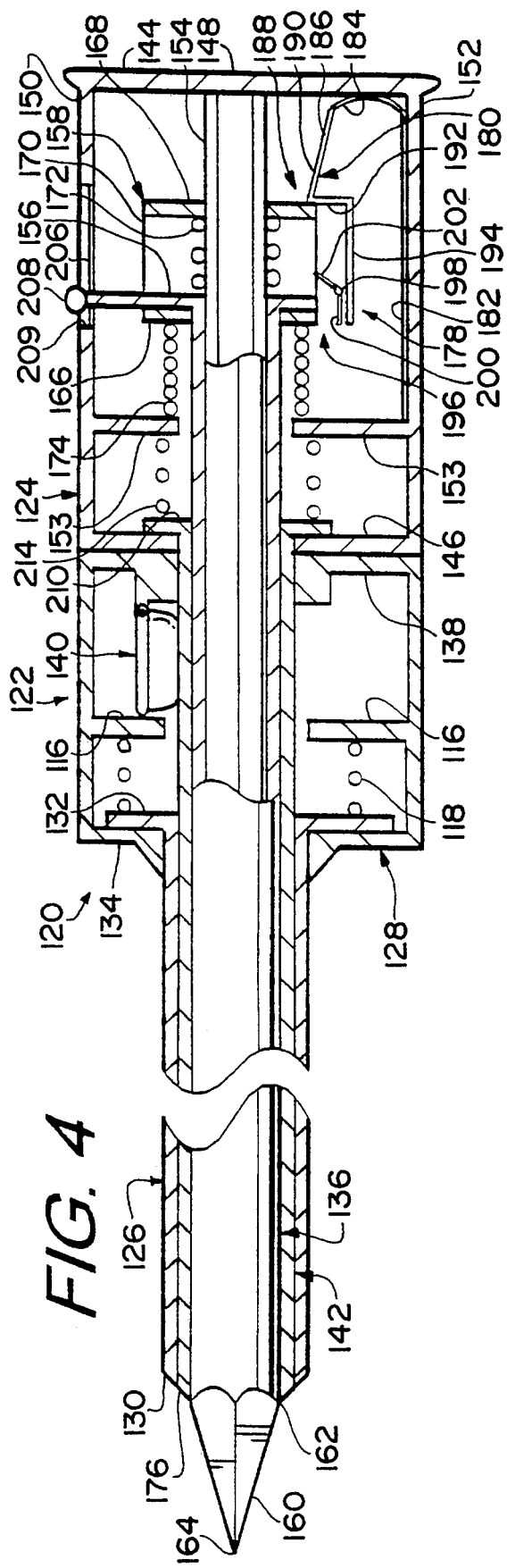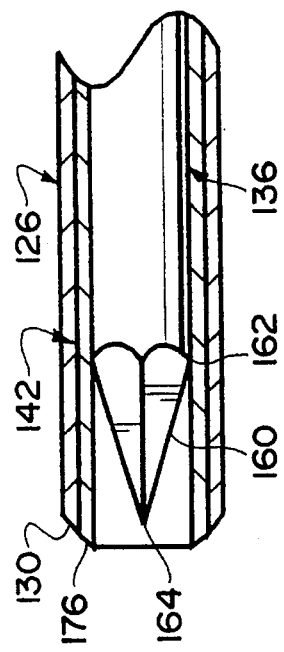

RETRACTABLE SAFETY PENETRATING INSTRUMENT WITH SAFETY SHIELD AND MULTIPLE TRIGGERING AND/OR MOVING COMPONENTS

CROSS-REFERENCE TO RELATED APPLICATIONS

This application is a continuation-in-part of pending applications Ser. No. 08/247,205, filed May 20, 1994, still pending and Ser. No. 08/254,007, filed Aug. 10, 1994, now U.S. Pat. No. 5,478,317, which are a divisional application and a continuation application, respectively, of application Ser. No. 07/800,507, filed Nov. 27, 1991 and now abandoned. The disclosures of the above patent applications are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While retracting safety penetrating instruments have been well received, there is room for improvement in easing penetration and minimizing the likelihood of the penetrating member being retracted before the portal sleeve has entered the anatomical cavity.

SUMMARY OF THE INVENTION

Accordingly, it is a primary object of the present invention to improve safety penetrating instruments of the type having a portal sleeve, a safety shield and a retractable penetrating member.

It is an additional object of the present invention to ease penetration of an anatomical cavity wall with a safety penetrating instrument by permitting penetrating components of the safety penetrating instrument, such as a portal sleeve, safety shield and/or penetrating member, to move proximally during penetration of the anatomical cavity wall and maintaining the movable penetrating components in substantially aligned positions such that a smooth distal profile is preserved during penetration of the anatomical cavity wall.

Another object of the present invention is to permit proximal movement of a safety shield and a penetrating member of a safety penetrating instrument in response to tissue contact during penetration of an anatomical cavity wall.

A further object of the present invention is to permit proximal movement of a safety shield and a portal sleeve of a safety penetrating instrument in response to tissue contact during penetration of an anatomical cavity wall.

Yet another object of the present invention is to permit proximal movement of a safety shield, portal sleeve and penetrating member of a safety penetrating instrument in response to tissue contact during penetration of an anatomical cavity wall.

A further object of the present invention is to trigger retraction of a penetrating member of a safety penetrating instrument in response to distally-biased movement of the penetrating member and a safety shield of the safety penetrating instrument upon entering an anatomical cavity.

An additional object of the present invention is to trigger retraction of a penetrating member of a safety penetrating instrument in response to distally-biased movement of a safety shield and portal sleeve of the safety penetrating instrument upon entering an anatomical cavity.

It is yet another object of the present invention to trigger retraction of a penetrating member of a safety penetrating instrument in response to distally-biased movement of the penetrating member and a portal sleeve of the safety penetrating instrument upon entering an anatomical cavity.

Still another object of the present invention is to trigger retraction of a penetrating member of a safety penetrating instrument in response to distally-biased movement of the penetrating member, safety shield and portal sleeve of the safety penetrating instrument upon entering an anatomical cavity.

Some of the advantages of the present invention over the prior art are that penetration of an anatomical cavity wall can be achieved using a smooth and continuous movement, that safe penetration of an anatomical cavity wall can be commenced with the portal sleeve and/or safety shield in an extended rest position either shielding or exposing the tip of the penetrating member, and that retraction of the penetrating member of the safety penetrating instrument can be conditioned on entry into an anatomical cavity of one or more of the penetrating components such that the safety and efficacy of the safety penetrating instrument is enhanced.

The present invention is generally characterized in a safety penetrating instrument for establishing a portal in the wall of an anatomical cavity including a housing, a portal sleeve fixedly secured to the housing, a penetrating member disposed within the portal sleeve and movable relative to the portal sleeve between an extended position where a distal end of the penetrating member protrudes distally from a distal end of the portal sleeve and a retracted position proximally spaced from the extended position, a distally-biased safety shield disposed between the portal sleeve and the penetrating member and movable relative to the portal sleeve between an extended safety shield rest position protecting the penetrating member distal end when the penetrating member is retracted and a safety shield retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position while permitting a predetermined amount of proximal movement of the penetrating member during penetration of the anatomical cavity wall, penetrating member bias means for biasing the penetrating member distally in the locked penetrating member extended position to permit the penetrating member to move proximally during penetration of the anatomical cavity wall and distally upon introduction into the anatomical cavity, and releasing means responsive to penetration of the safety penetrating instrument into the anatomical cavity for triggering release of the locking means to permit the retracting means to move the penetrating member to the penetrating member retracted position.

Another aspect of the present invention is generally characterized in a safety penetrating instrument for establishing a portal in the wall of an anatomical cavity including a housing, a distally-biased portal sleeve movable relative to the housing between an extended rest position and a proximally spaced retracted position, a penetrating member disposed within the portal sleeve and movable relative to the portal sleeve between an extended position and a retracted position proximally spaced from the extended position, a distally-biased safety shield disposed between the portal sleeve and the penetrating member and movable relative to the penetrating member between an extended safety shield rest position protecting the penetrating member distal end when the penetrating member is retracted and a safety shield retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position and preventing proximal movement of the penetrating member during penetration of the anatomical cavity wall, and releasing means responsive to penetration of the safety penetrating instrument into the anatomical cavity for triggering release of the locking means to permit the retracting means to move the penetrating member proximally to the penetrating member retracted position.

Yet another aspect of the present invention is generally characterized in a safety penetrating instrument for establishing a portal in the wall of an anatomical cavity including a housing, a distally-biased portal sleeve movable relative to the housing between an extended rest position and a proximally spaced retracted position, a penetrating member disposed within the portal sleeve and movable relative to the portal sleeve between an extended position and a retracted position proximally spaced from the extended position, a distally-biased safety shield disposed between the portal sleeve and the penetrating member and movable relative to the penetrating member between an extended safety shield rest position protecting the penetrating member distal end when the penetrating member is retracted and a safety shield retracted position exposing the penetrating member distal end when the penetrating member is extended, retracting means for moving the penetrating member from the penetrating member extended position to the penetrating member retracted position, means for manually moving the penetrating member from the penetrating member retracted position to the penetrating member extended position, locking means for locking the penetrating member in the penetrating member extended position while permitting a predetermined amount of proximal movement of the penetrating member during penetration of the anatomical cavity wall, penetrating member bias means for biasing the penetrating member distally in the locked penetrating member extended position to permit the penetrating member to move proximally during penetration of the anatomical cavity wall and distally upon introduction into the anatomical cavity, and releasing means responsive to penetration of the safety penetrating instrument into the anatomical cavity for triggering release of the locking means to permit the penetrating member retracting means to move the penetrating member proximally to the penetrating member retracted position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference numeral or by reference numerals sharing the same last two digits.

BRIEF DESCRIPTION OF THE DRAWINGS

FIG. 4 is a broken side view, partly in section, of a modification of a safety penetrating instrument according to the present invention.

FIG. 5 is a fragmentary side view, partly in section, of the distal end of the safety penetrating instrument of FIG. 4 following penetration into an anatomical cavity.

DESCRIPTION OF THE PREFERRED EMBODIMENTS

Figure 1:
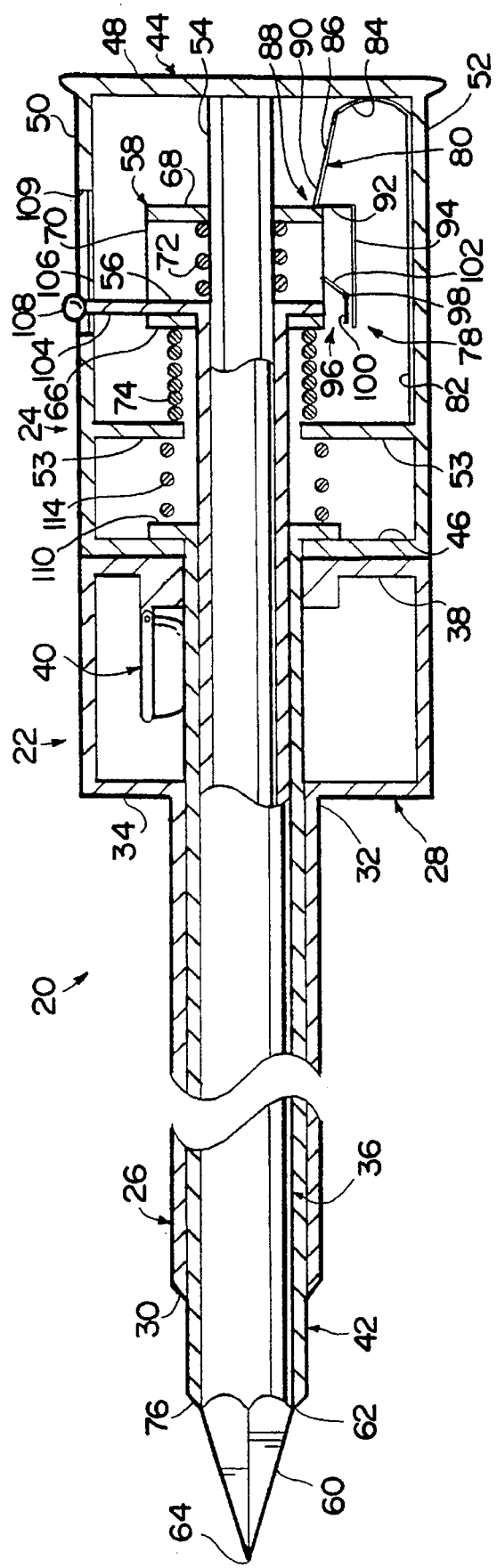
FIG. 1 is a broken side view, partly in section, of a safety penetrating instrument according to the present invention.

A safety penetrating instrument 20 according to the present invention, as shown in FIG. 1, includes a portal unit 22 and a penetrating unit 24. The portal unit 22 includes an elongate portal sleeve 26 and a housing 28 mounting a proximal end of portal sleeve 26. Portal sleeve 26 terminates distally at a distal end 30 and proximally at a proximal end 32 secured to front wall 34 of housing 28 and can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 36 of penetrating unit 24.

Housing 28 can be made of any desirable material and can have any desirable configuration to facilitate grasping by a surgeon and includes a rear wall 38 having an opening therein aligned with an opening in the housing front wall 34 to allow passage therethrough by the penetrating member 36. The housing 28 is preferably constructed to sealingly engage instruments passing therethrough and to include a valve biased to a closed state when no instrument passes through the portal sleeve. A flapper valve 40 is shown; however, any suitable valve construction can be utilized, including trumpet or nipple valves.

Penetrating unit 24 includes penetrating member 36, a safety shield 42 and a hub 44 mounting proximal ends of the penetrating member and the safety shield. Hub 44 includes longitudinally spaced front and rear walls 46 and 48, laterally spaced top and bottom walls 50 and 52, and an inner wall or partition 53 proximally spaced from the front wall of the hub. Hub front wall 46 has a configuration to mate with the rear wall 38 of the housing; and, when the hub is mated with the housing as shown, safety shield 42 is disposed between penetrating member 36 and portal sleeve 26. Penetrating member 36 has an elongate shaft or body which is at least partly hollow and is telescopically fitted over a guide tube 54 extending distally from hub rear wall 48. The penetrating member terminates proximally at a transverse flange 56 disposed between walls of a rail member 58 mounted in hub 44 and has a tapered distal end 60 extending from a transverse dimensional transition or junction 62 in the shaft or body and terminating at a sharp distal tip 64.

Rail member 58 is generally U-shaped including a forward wall 66 disposed transverse or perpendicular to a longitudinal axis of the penetrating instrument, a rearward wall 68 in configuration parallel to forward wall 66 and a side wall 70 transversely joining the forward and rearward rail member walls. Flange 56 is disposed between the rail member forward and rearward walls with the rail member forward wall 66 having an opening therein allowing passage therethrough by the penetrating member 36. The rail member forward and rearward walls are disposed parallel or substantially parallel to flange 56, and a bias member 72 is connected between penetrating member flange 56 and the rail member rearward wall 68 to bias the penetrating member distally. As shown, bias member 72 includes a helical coil spring disposed around the guide tube 54 and mounted in compression between flange 56 and the rail member rearward wall 68 to bias the penetrating member 36 distally to cause flange 56 to abut the rail member forward wall 66. However, bias member 72 can include various other types of springs as well as other types of bias devices including compression springs, tension springs, torsion springs, pan springs, leaf springs, rubber, plastic or magnets, for example.

A retracting member 74 is mounted between rail member forward wall 66 and the inner wall 53 of hub 44 to bias the penetrating member 36 in a proximal direction to a retracted position where the distal end 60 of the penetrating member is disposed proximally of the safety shield distal end 76 as will be explained further below. The retracting member 74 includes a helical coil spring disposed around the penetrating member 36 and mounted in compression between the rail member forward wall 66 and the hub inner wall 53 to bias the rail member 58 and, therefore, the penetrating member 36, in a proximal direction to the retracted position where the distal end 60 of the penetrating member is disposed proximally of the distal end 76 of the safety shield 42.

A locking and releasing mechanism 78 for locking the penetrating member in an extended position, shown in FIG. 1, exposing the distal end 60 of the penetrating member and for releasing the rail member 58 to allow the penetrating member 36 to move to the retracted position includes a latch or locking spring 80, made of a strip of resilient material, formed to have a substantially flat base 82 secured to the bottom wall 52 of hub 44 and a bend 84 joining the proximal end of the base 82 with an upwardly angled arm 86 spaced from the base. Arm 86 carries or forms a latch 88 having a proximal angled latching surface 90 joining a distal latching surface 92 disposed substantially transverse to the longitudinal axis of the safety penetrating instrument and substantially parallel to the rail member rearward wall 68. Arm 86 has an extension 94 positioned distally of latch 88, and a releasing member or trigger 96 is juxtaposed with extension 94. The trigger 96 is pivotally mounted in the hub on a pin 98 secured to a wall or walls of the hub or structure supported in the hub, and the trigger is generally L-shaped with a leg 100 overlying extension 94 and a leg 102 extending transversely from leg 100 but at a slight angle toward the proximal end of the safety penetrating instrument. A torsion spring (not shown) is coiled around pin 98 and fixed to trigger 96 to bias the trigger counterclockwise, looking at FIG. 1, such that leg 100 is biased toward extension 94.

The penetrating member flange 56 extends toward the top wall 50 of the hub and a post 104 extends from the penetrating member flange through a longitudinal slot 106 formed in the top wall of the hub to terminate at a handle 108 disposed within an elongate trough-like recess 109. Handle 108, which can be coupled with the penetrating member directly as shown or via the rail member, can be grasped and manually moved distally along the slot formed in the top wall of the hub to move the penetrating member from the retracted position to the locked extended position as previously explained above.

Safety shield 42 extends from distal end 76 to a proximal flange 110 disposed between the hub forward wall 46 and the inner wall or partition 53 proximally spaced from the hub forward wall. A bias member 114 in the form of a helical coil spring is disposed around the penetrating member 36 and held in compression between the safety shield flange 110 and the hub inner wall 53 to bias the safety shield 42 distally toward a rest position where the safety shield flange abuts the hub forward wall.

The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 44 can be coupled to the housing 28 by suitable detent or latch mechanisms if desired, and the penetrating unit can be withdrawn from the portal unit leaving the portal sleeve 26 in place within an anatomical cavity to serve as a portal for the introduction of medical instruments therethrough.

Figure 3:
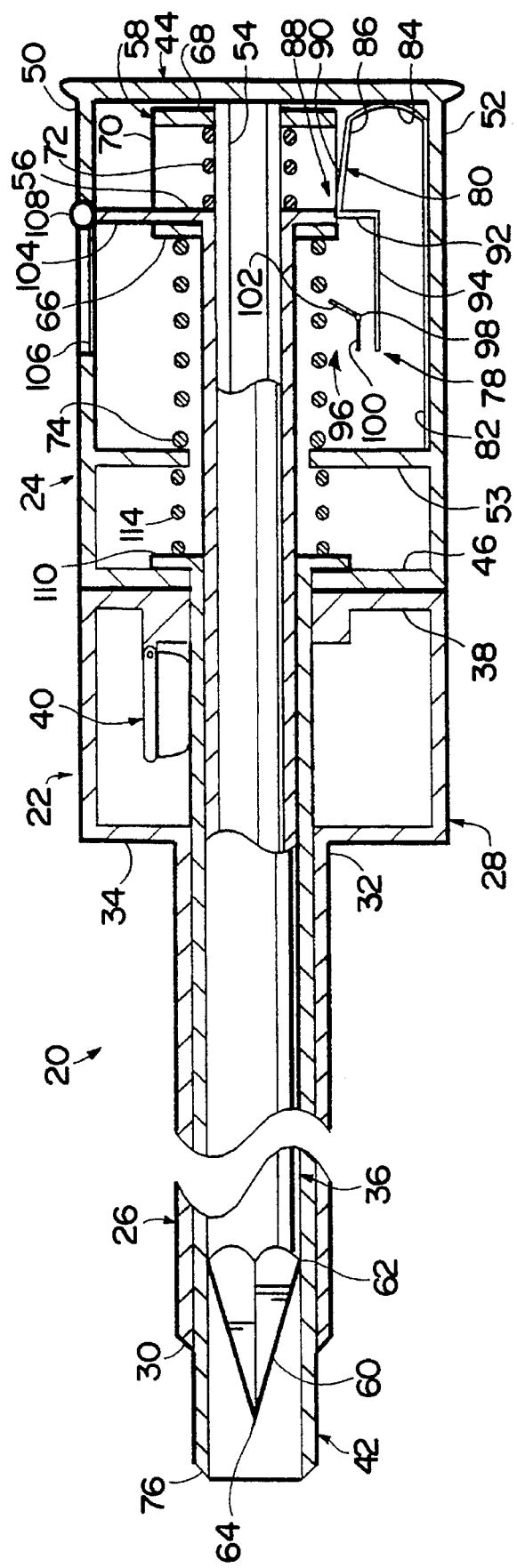
FIG. 3 is a broken side view, partly in section, of the safety penetrating instrument of FIG. 1 following penetration into the anatomical cavity.

In use, the safety penetrating instrument 20 can be provided in the condition illustrated in FIG. 3 with the safety shield 42 in the extended rest position and the penetrating member 42 in the retracted position such that the distal end 60 of the penetrating member is proximally spaced from the distal end 76 of the safety shield to protect the sharp tip 64 of the penetrating member prior to use. In order to move the penetrating member to the extended position shown in FIG. 1, the handle 108 is grasped to move the penetrating member 36, and thus the rail member 58, distally until the rail member rearward wall 68 rides over latch 88 to be latched in the extended position with the rail member rearward wall 68 locked against distal latching surface 92. The user can feel the rail member rearward wall 68 lock into place in engagement with the latch 88 and can also visually determine that the penetrating member is in the locked extended position by noting the position of the handle 108 at a distal end of the slot 106.

Figure 2:
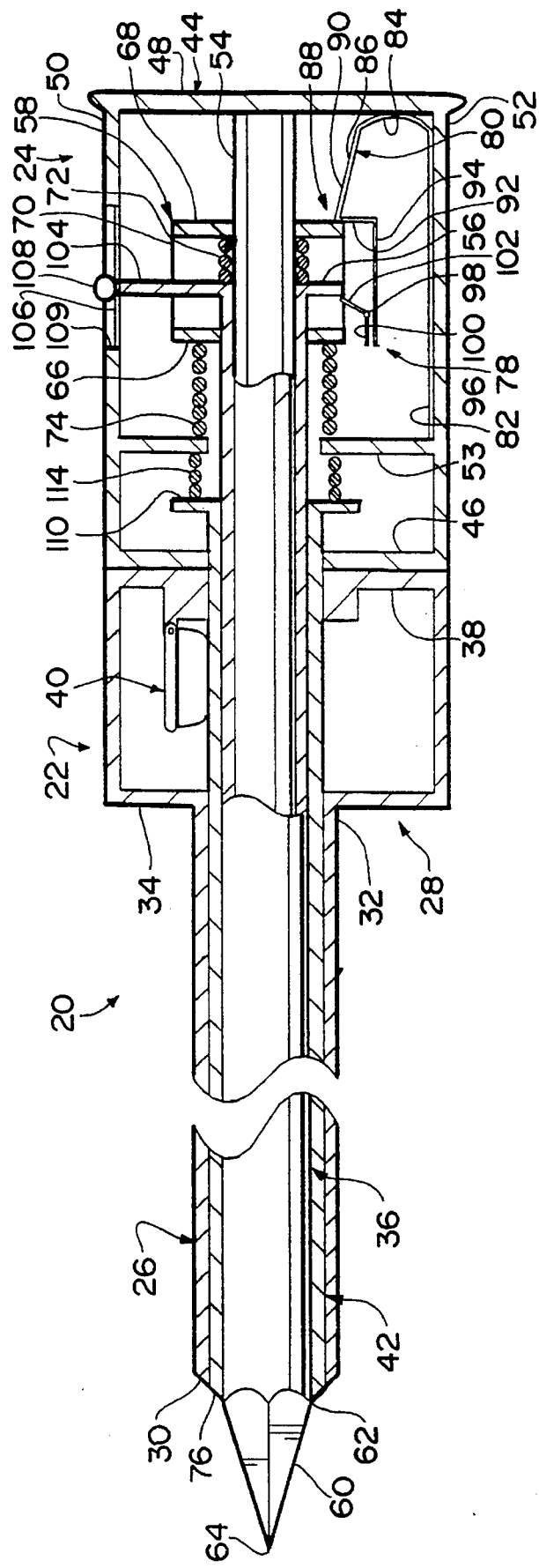
FIG. 2 is a broken side view, partly in section, of the safety penetrating instrument of FIG. 1 during penetration of a wall of an anatomical cavity.

With the penetrating member 36 locked in the extended position illustrated in FIG. 1, the safety shield distal end 76 can be disposed proximally of the distal tip 64 of the penetrating member in alignment with the transverse dimensional transition or junction 62 to present a smooth profile for penetrating tissue. Portal sleeve distal end 30 is fixed and is proximally spaced from the safety shield distal end 76 a predetermined distance approximately equal to the distance between the partition and the hub front wall and between the rail member walls. Penetrating member 36 can move proximally against the bias of bias member 72 in the extended position in response to forces acting on the penetrating member distal end, such as the force from tissue contact during penetration of an anatomical cavity wall. Proximal movement of the penetrating member is limited by engagement of the penetrating member flange 56 with the rearward wall 68 of the rail member, which serves as a stop or abutment. Similarly, safety shield 42 can move proximally against the bias of bias member 114 in response to forces acting on the safety shield distal end 76 until the safety shield flange 110 abuts the hub partition 53. Since both the safety shield and the penetrating member are free to move proximally in response to tissue resistance during penetration, the alignment of the safety shield distal end with the penetrating member junction can be substantially maintained in order to ease penetration. When penetration of an anatomical cavity wall is commenced, therefore, the force from tissue contact on the safety shield and penetrating member distal ends 76 and 60 will cause the safety shield and penetrating member to move together proximally against the bias of respective bias members 114 and 72 towards becoming aligned with the portal sleeve distal end 30. Penetrating member flange 56 will also move past trigger leg 102 but will not cause movement of latch 88 since clockwise rotation of the trigger does not bring trigger leg 100 into contact with arm extension 94; and, since trigger 96 is biased in a counterclockwise direction, flange 56 will be positioned proximally of trigger leg 102 as shown in FIG. 2.

Upon entry into the anatomical cavity, the counterforce on the safety shield and penetrating member distal ends caused by tissue contact will be reduced allowing bias members 114 and 72 to move the safety shield and penetrating member distally. Distal movement of the penetrating member causes flange 56 to engage trigger leg 102 and to pivot the trigger counterclockwise looking at FIG. 2 causing leg 100 to engage arm extension 94. The engagement of leg 100 with arm extension 94 causes arm 86 to move toward base 82 moving the latch 88 out of engagement with the rail member rearward wall 68 thereby allowing the retracting member 74 to cause the penetrating member to move proximally to the retracted position wherein the penetrating member distal end 60 is proximally spaced from the safety shield distal end 76 to protect the sharp tip 64 of the penetrating member as shown in FIG. 3. The penetrating unit 24 including the penetrating member 36 can then be withdrawn from the portal unit 22 leaving the portal sleeve 26 in place within the anatomical cavity wall to serve as a portal for introducing medical instruments therethrough.

A modification of the safety penetrating instrument of the present invention is shown in FIG. 4 at 120. The modified safety penetrating instrument 120 includes a penetrating unit 124 identical to penetrating unit 24 for safety penetrating instrument 20 and a portal unit 122 similar to portal unit 22 but with a distally-biased portal sleeve 126. Housing 128 for portal unit 122 is similar to housing 28 but with an inner wall or partition 116 proximally spaced from the front wall 134 of the housing. Portal sleeve 126 terminates proximally at a flange 132 disposed between the front wall 134 of the housing 128 and the inner wall or partition 116. A bias member 118 in the form of a helical coil spring is disposed around the safety shield 142 and held in compression between the portal sleeve flange 132 and the housing partition 116 to bias the portal sleeve distally toward a rest position where the portal sleeve flange 132 abuts the front wall 134 of the housing and the distal end 130 of the portal sleeve is aligned with the distal end 176 of the safety shield and the junction 162 of the extended penetrating member 136.

Use of the safety penetrating instrument 120 for penetrating an anatomical cavity wall proceeds essentially as described above for safety penetrating instrument 20 with the exception that the portal sleeve 126 will move proximally in response to tissue contact and distally upon entering the anatomical cavity. Prior to contacting the anatomical cavity wall, the penetrating member 136 is manually moved distally to be locked in the extended position and distal ends 130 and 176 of the portal sleeve 126 and safety shield 142 are in rest positions aligned with the junction 162 at the distal end of the extended penetrating member as shown in FIG. 4. During penetration, the portal sleeve 126, penetrating member 136 and safety shield 142 are moved proximally due to the force from tissue contact such that the smooth distal profile can be maintained in order to ease penetration. Upon penetrating into the anatomical cavity, the counterforce on the distal ends of the portal sleeve, penetrating member and safety shield are reduced allowing the respective bias members to move the portal sleeve, penetrating member and safety shield distally. As shown, distally-biased movement of the penetrating member triggers release of the penetrating member from the locked extended position allowing the penetrating member to be moved proximally to a retracted position where the distal end of the penetrating member is proximally spaced from both the portal sleeve and safety shield distal ends as shown in FIG. 5.

Figure 6:
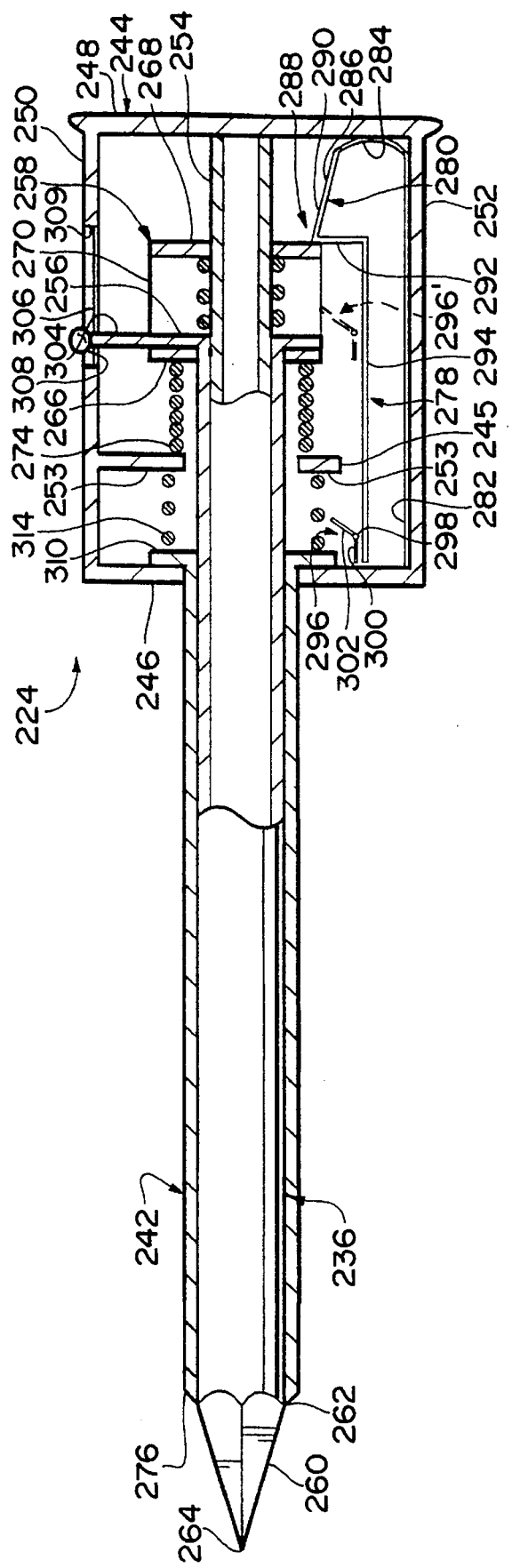
FIG. 6 is a broken side view, partly in section, of a modified penetrating unit for the safety penetrating instrument according to the present invention.

A modified penetrating unit for use with the safety penetrating instruments of the present invention is shown in FIG. 6 at 224. The modified penetrating unit 224 includes a hub 244 mounting proximal ends of a penetrating member 236 and a safety shield 242. Hub 244 is similar to hub 44 for safety penetrating instrument 20 but with an opening or gap 245 formed in the hub partition 253 on the side of the hub mounting a locking and releasing mechanism 278. Arm extension 294 for penetrating unit 224 extends distally from a distal latching surface 292 through the opening 245 to be disposed alongside the safety shield flange 310. A trigger 296, similar to trigger 96 for safety penetrating instrument 20, is distally spaced from hub partition 253 and is pivotally mounted on a pin 298 secured to a wall or walls of the hub between arm extension 294 and the safety shield flange 310. Trigger 296 is generally L-shaped with a leg 300 overlying extension 294 and a leg 302 extending transversely from leg 300 and toward the proximal end of the hub to be disposed proximally of the safety shield flange 310 when the safety shield is in the extended rest position shown.

Prior to use, penetrating unit 224 can be coupled with a portal unit, such as portal unit 22, for establishing a portal in the wall of an anatomical cavity. Operation of the penetrating unit 224 is similar to that of penetrating unit 24 with the exception that distally-biased movement of the safety shield 242 in response to a reduction in force caused by tissue contact is used to trigger release of the latch 288 from the rail member rearward wall 268 so that the penetrating member 236 is moved proximally to the retracted position when the safety shield enters the anatomical cavity.

Another modification of the penetrating unit of the safety penetrating instrument according to the present invention is arrived at by mounting a second trigger in the penetrating unit 224, as shown in phantom at 296' in FIG. 6. The second trigger 296' is mounted within the hub 244 at a location similar to that of trigger 96 in penetrating unit 24 for being engaged by the penetrating member flange 256. By providing a second trigger proximate the penetrating member flange 256, movement of the penetrating member to the retracted position can be achieved in response to distally-biased movement of either or both of the safety shield and the penetrating member upon entering an anatomical cavity. Operation of the modified penetrating unit is similar to that described above in connection with penetrating unit 224 with the exception that safety shield and penetrating member flanges are moved to positions proximally spaced from triggers 296 and 296' during penetration of an anatomical cavity wall and will move distally in response to a reduction in force from tissue contact upon entering the anatomical cavity. Distally-biased movement of either or both of the safety shield 242 and penetrating member 236 causes one or both triggers to be rotated counterclockwise looking at FIG. 6 such that arm extension 294 of the locking spring 280 will be moved away from the longitudinal axis of the penetrating unit toward the base 282 of the locking spring to release latch 288 from the rail member 258. Retraction of the penetrating member can thus be assured even if one of the penetrating components is prevented from moving distally upon entering the anatomical cavity.

Figure 7:
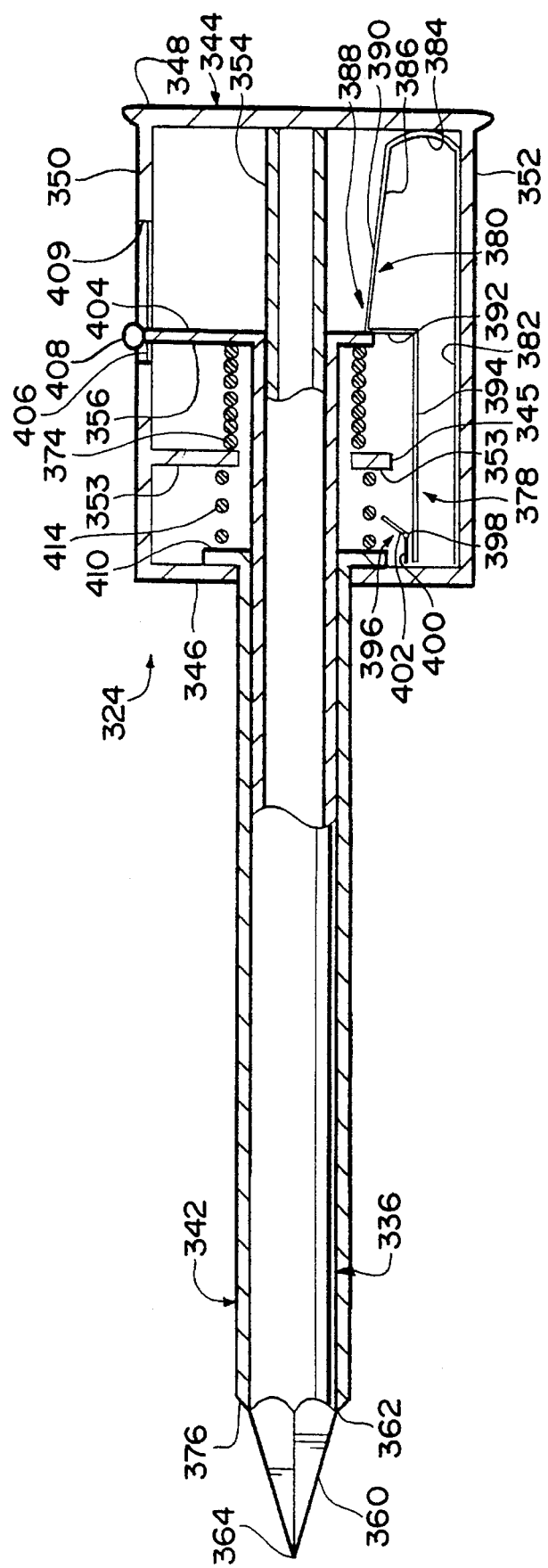
FIG. 7 is a side view, partly in section, of still another modified penetrating unit for the safety penetrating instrument according to the present invention.

FIG. 7 illustrates another modified penetrating unit for a safety penetrating instrument according to the present invention wherein the modified penetrating unit 324 is similar to penetrating unit 224 described above but with a locking mechanism that prevents proximal movement of the penetrating member in response to tissue contact during penetration of an anatomical cavity wall. The locking spring 380 of the locking and releasing mechanism 378 for penetrating unit 324 is the same as locking spring 280 for penetrating unit 224; however, the penetrating member 336 is not mounted by a rail member and is instead directly engaged by distal latching surface 392 formed by the locking spring 380. Retracting member 374 for penetrating unit 324 is disposed around the penetrating member 336 and is held in compression between the inner wall 353 of the hub 344 and the penetrating member flange 356 to bias the penetrating member proximally against latching surface 392 when the penetrating member is in the extended position shown and to move the penetrating member to the retracted position when the latch 388 is released. As a result, penetrating member 336 is fixed during penetration and will move proximally to the retracted position only in response to distally-biased movement of the safety shield 342 upon entering the anatomical cavity.

Figure 8:
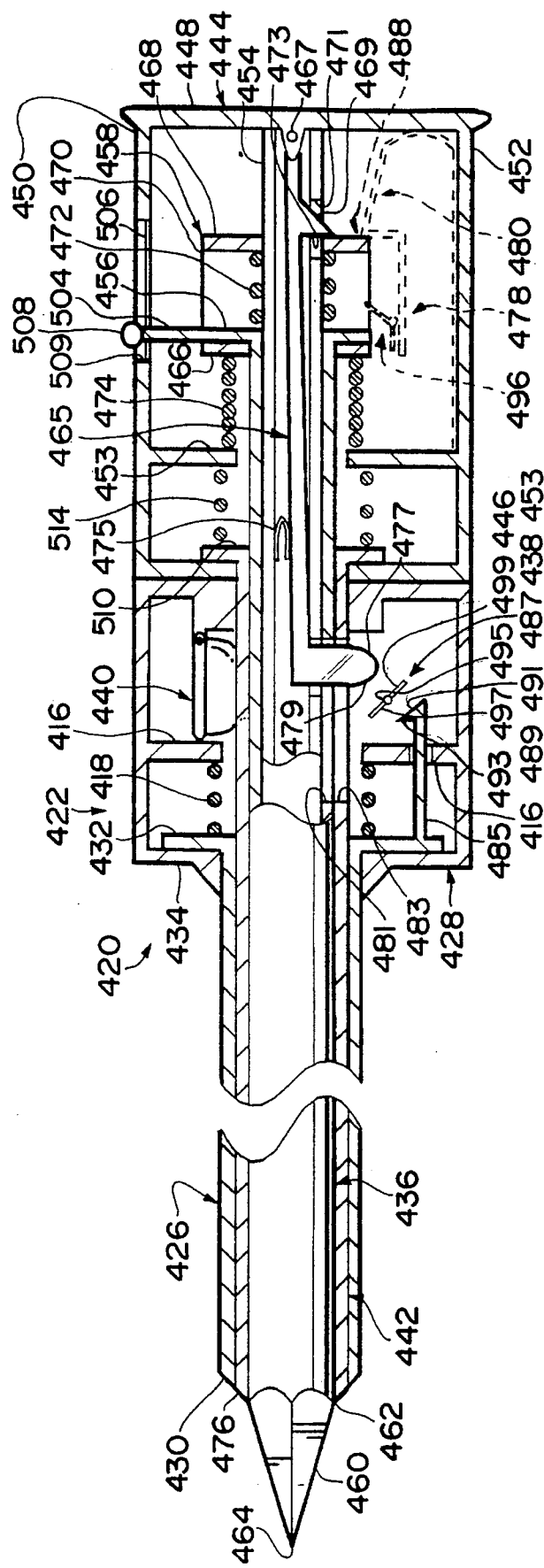
FIG. 8 is a broken side view, partly in section, of a further modification of a safety penetrating instrument according to the present invention.

Still another modification of the safety penetrating instrument according to the present invention is illustrated in FIG. 8 at 420. The modified safety penetrating instrument 420 is similar to safety penetrating instrument 20 except that movement of the penetrating member to the retracted position is triggered by distally-biased movement of the portal sleeve in response to a reduction in the force from tissue contact following entry into the anatomical cavity. Safety penetrating instrument 420 includes a portal unit 422 and a penetrating unit 424 having a penetrating member 436, a safety shield 442 and a hub 444 mounting proximal ends of the penetrating member and the safety shield. Penetrating member 436 is similar to penetrating member 36 and terminates distally at a distal end 460 and proximally at a transverse flange 456 disposed between forward and rearward walls 466 and 468 of a rail member 458. The proximal end of the penetrating member 436 also includes a hollow portion telescopically fitted over a guide tube 454 extending distally from the rear wall 448 of the hub 444. The bias member 472 is similar to bias member 72 and is disposed around the guide tube 454 and held in compression between the penetrating member flange 456 and the rearward wall of rail member 458. A retracting member 474, similar to retracting member 74, is disposed around the penetrating member 436 and is held in compression between the rail member forward wall 466 and hub inner wall 453.

Rail member 458 is locked in the extended position shown in FIG. 8 by a longitudinal latch arm 465 disposed within the guide tube 454 and having a proximal end pivotally mounted on a pin 467 secured to the rear wall 448 of the hub. Latch arm 465 carries a latching protrusion 469 in opposed relation to a slot 471 formed in the guide tube 454. Protrusion 469 is generally triangular with a transverse latching surface 473 configured to extend through slot 471 formed in the guide tube 454 to engage the rail member rearward wall 468. A leaf spring 475 is connected between the latch arm 465 and an inner surface of the guide tube 454 to bias the arm 465 in a counterclockwise direction looking at FIG. 8 toward an engaged position where latching protrusion 469 extends through the slot 471 formed in the guide tube. A triggering protrusion 477 is formed at a distal end of the latch arm 465 and includes a curved distal edge or surface 479 that protrudes through aligned slots 481 and 483 formed in the guide tube 454 and the penetrating member 436 distally of slot 471 to communicate into housing 428.

Penetrating member slot 481 is sufficiently long to allow back and forth movement of the penetrating member 436 within the rail member 458.

Portal unit 422 is similar to portal unit 22 for safety penetrating instrument 20 and, in addition, includes a finger 485 extending perpendicularly from the portal sleeve flange 432 in a proximal direction and a lever 487 disposed between finger 485 and triggering protrusion 477. Finger 485 extends through an opening formed in the housing partition 416 and terminates proximally in a barb or pawl 489 with an acutely angled leading edge 491 and a vertical trailing edge 493 parallel to flange 432. Lever 487 is pivotally mounted on a pin 495 secured to a wall or walls of housing 428 perpendicular to the longitudinal axis of the penetrating instrument, and includes axially opposed ends 497 and 499. Finger 485 is positioned on flange 432 in a manner to engage lower end 499 of lever 487 when moved proximally. Upper end 497 of lever 487 is rotatable in a clockwise direction to contact triggering protrusion 477.

Use of the safety penetrating instrument 420 is similar to that described above with respect to safety penetrating instrument 20 in that, when the user desires to penetrate into an anatomical cavity, the safety penetrating instrument will normally be provided with the penetrating member 436 in the retracted position where the distal end 460 of the penetrating member is proximally spaced from the portal sleeve distal end 430 and the safety shield distal end 476. Additionally, the portal sleeve 426 and safety shield 442 will be provided in rest positions where the portal sleeve flange 432 abuts the housing front wall 434 and the safety shield flange 510 abuts the hub front wall 446. Furthermore, latching protrusion 469 of latch arm 465 will be disposed distally of the rail member rearward wall 468 and barb 489 of finger 485 will be disposed distally of lever lower end 499. The penetrating member 436 is biased to the retracted position by retracting member 474 with handle 502 being disposed at a proximal end of the slot 500 in the hub 444.

Prior to commencing penetration of an anatomical cavity wall, handle 502 is grasped and manually moved distally to move penetrating member 436 distally against the bias of retracting member 474 until the rail member rearward wall 468 rides over the latching protrusion 469 by engaging an angled proximal surface of the latching protrusion 469 to move the latch arm 465 clockwise looking at FIG. 8. When rail member rearward wall 468 moves distally past latching surface 473, latch arm 465 springs back in a counter-clockwise direction to lock the rail member 458 and penetrating member 436 mounted thereby in the extended position shown. As previously noted, the user can feel the rail member lock into place in engagement with latch arm 465 and can also visually determine that the penetrating member is in the locked extended position by noting the position of the handle 502 at a distal end of the slot. With the penetrating member 436 locked in the extended position, penetrating member flange 456 will be distally biased by bias member 472 into abutting relation with the rail member forward wall 466. The portal sleeve flange 432 will be distally biased by bias member 438 into abutment with housing forward wall 434 such that the distal end 430 of the portal sleeve will be disposed adjacent the transverse dimensional transition or junction 452 of the penetrating member 436. Also, the safety shield flange 510 will be distally biased by bias member 514 into abutment with hub front wall 446 such that the distal end 476 of the safety shield will be disposed adjacent the transverse dimensional transition or junction of the penetrating member.

With the safety penetrating instrument 420 in the position illustrated in FIG. 8, penetration of the anatomical cavity wall is commenced, and the force from tissue contact on the portal sleeve, safety shield and penetrating member distal ends 430, 476 and 448 will cause the portal sleeve, safety shield and penetrating member to move together proximally against the bias of springs 438, 514 and 462, respectively. Proximal movement of the portal sleeve 426 also causes barb 489 carried by finger 485 to contact and move past lever lower end 499 causing lever 487 to rotate counter-clockwise. Lever upper end 497 is thus moved away from triggering protrusion 477 without causing any movement of latch arm 465. Accordingly, the barb 489 will then be positioned proximally of the lever lower end 499. Upon entry into the anatomical cavity, the counterforce on the distal end of the portal sleeve will be reduced allowing spring 438 to move the portal sleeve distally causing barb 489 to engage lever lower end 499 and thereby to pivot the lever 487 clockwise causing lever upper end 497 to engage triggering protrusion 477. The engagement of lever 487 with triggering protrusion 477 causes latch arm 465 to rotate clockwise, looking at FIG. 8, moving the latching protrusion 469 out of engagement with rail member rearward wall 468 thereby allowing retracting member 474 to cause the penetrating member to move proximally to the retracted position, such as shown in FIG. 5, wherein the penetrating member distal end 460 is proximally spaced from the distal end 430 of the portal sleeve 426 to protect the sharp tip 464 of the penetrating member. The penetrating unit 424 can then be withdrawn from the portal unit 422 leaving the portal sleeve 426 in place for the introduction of medical instruments therethrough.

Another modification of the safety penetrating instrument of the present invention is arrived at by combining the locking and releasing mechanisms of safety penetrating instruments 20 and 420 to permit movement of the penetrating member to the retracted position in response to distally-biased movement of both the portal sleeve and penetrating member. The modification involves mounting a locking and releasing mechanism such as locking and releasing mechanism 70 for engaging the rail member 458 in hub 444 of safety penetrating instrument 420 as shown in phantom at 470 in FIG. 8. Use of the modified safety penetrating instrument is similar to that described above in connection with safety penetrating instruments 20 and 420 with the exception of both the latch spring 472 and latch arm 465 must be disengaged in order for the penetrating member 436 to be moved proximally to the retracted position.

It will also be appreciated that an opening, like opening 245, can be formed in the hub partition 553 and a locking and releasing mechanism like locking and releasing mechanism 278 can be mounted in the hub 444 to permit retraction of the penetrating member in response to distally-biased movement of the portal sleeve, safety shield and/or penetrating member of the safety penetrating instrument.

Figure 9:
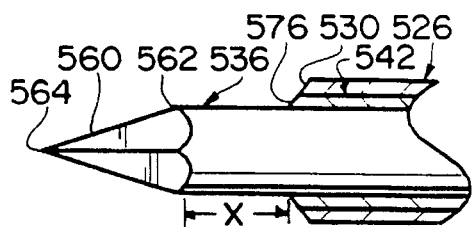
FIGS. 9–13 are fragmentary side views, partly in section, illustrating alternative distal configurations for the safety penetrating instruments of the present invention.

FIG. 9 shows an alternative distal configuration for the safety penetrating instruments of the present invention wherein the distal end 576 of the safety shield 542 and the distal end 530 of the portal sleeve 526 are proximally spaced from the distal end junction 562 of the penetrating member 536 a predetermined distance x when the safety shield and portal sleeve are in rest positions and the penetrating member is locked in the extended position. In this configuration, the penetrating member can move proximally during penetration towards becoming aligned with the safety shield distal end and portal sleeve distal end to ease penetration by providing a smooth profile and can either stop or move together with the safety shield and portal sleeve as penetration continues. Upon entering into an anatomical cavity, the safety shield, penetrating member and/or portal sleeve can spring back distally triggering release of the latch holding the penetrating member to permit the retracting member to move the penetrating member proximally to the retracted position where the sharp tip 564 of the penetrating member is protected.

Figure 10:
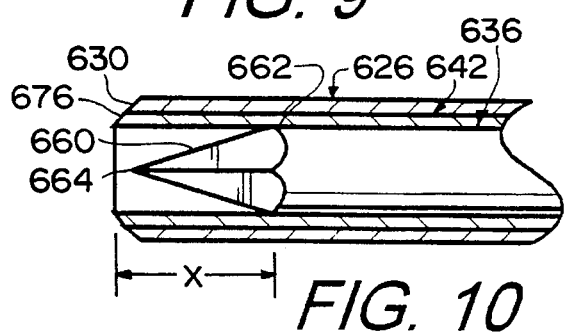

Another distal configuration for the safety penetrating instruments of the present invention is shown in FIG. 10 wherein the distal end 630 of the portal sleeve 626 and the distal end 676 of the safety shield 642 are distally spaced from the distal end junction 662 of the penetrating member 636 a predetermined distance x when the portal sleeve and safety shield are in rest positions and the penetrating member is locked in the extended position. In this configuration, the portal sleeve and safety shield can move proximally during penetration towards becoming aligned with the penetrating member distal end junction to ease penetration by providing a smooth profile and can move together with the penetrating member as penetration continues. Upon entering into an anatomical cavity, the penetrating member, safety shield and/or portal sleeve can spring back distally triggering release of the latch holding the penetrating member to permit the retracting member to move the penetrating member proximally to the retracted position where the sharp tip 664 of the penetrating member is protected.

Figure 11:
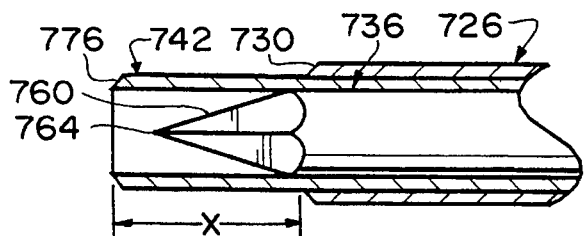

Still another distal configuration for the safety penetrating instruments of the present invention is shown in FIG. 11 wherein the distal end 776 of the safety shield 742 is distally spaced from the portal sleeve distal end 730 and the distal end junction 762 of the penetrating member 736 a predetermined distance x when the portal sleeve and safety shield are in rest positions and the penetrating member is locked in the extended position. In this configuration, the safety shield can move proximally during penetration towards becoming aligned with the portal sleeve distal end and the penetrating member distal end junction to ease penetration by providing a smooth profile and can move together with the penetrating member and/or portal sleeve as penetration continues. Upon entering into an anatomical cavity, the penetrating member, portal sleeve and/or safety shield can spring back distally triggering release of the latch holding the penetrating member to permit the retracting member to move the penetrating member proximally to the retracted position where the sharp tip 764 of the penetrating member is protected.

Figure 12:
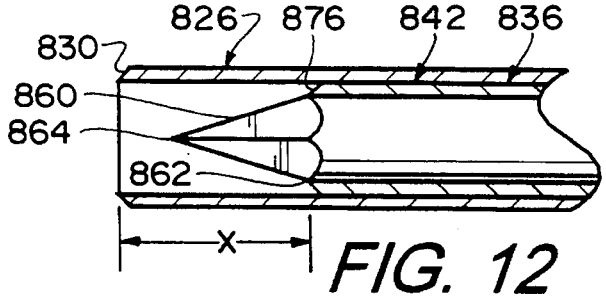

Yet another distal configuration for the safety penetrating instruments of the present invention is shown in FIG. 12 wherein the distal end 830 of the portal sleeve 826 is distally spaced from the distal end 876 of the safety shield 842 and the junction 862 of the penetrating member 836 a predetermined distance x when the portal sleeve and safety shield are in rest positions and the penetrating member is locked in the extended position. In this configuration, the portal sleeve can move proximally during penetration towards becoming aligned with the safety shield distal end and the penetrating member distal end junction to ease penetration by providing a smooth profile and can move together with the safety shield and penetrating member as penetration continues. Upon entering into an anatomical cavity, the penetrating member, safety shield and/or portal sleeve will spring back distally triggering release of the latch holding the penetrating member to permit the retracting member to move the penetrating member proximally to the retracted position where the sharp tip 864 of the penetrating member is protected.

Figure 13:
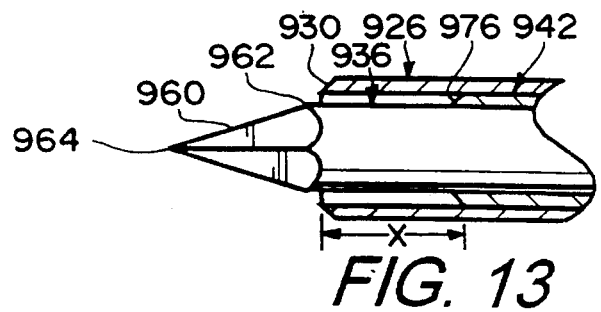

An additional distal configuration for the safety penetrating instruments of the present invention is shown in FIG. 13 wherein the distal end 976 of the safety shield 942 is proximally spaced from the distal end 930 of the portal sleeve 926 and the junction 962 of the penetrating member 936 a predetermined distance x when the portal sleeve and safety shield are in rest positions and the penetrating member is locked in the extended position. In this configuration, the penetrating member and portal sleeve can move proximally during penetration towards becoming aligned with the safety shield distal end to ease penetration by providing a smooth profile and can move together with the safety shield as penetration continues. Upon entering into an anatomical cavity, the penetrating member, safety shield and/or portal sleeve will spring back distally triggering release of the latch holding the penetrating member to permit the retracting member to move the penetrating member proximally to the retracted position where the sharp tip 964 of the penetrating member is protected.

From the above, it will be appreciated that multiple penetrating components of the safety penetrating instrument of the present invention are movable proximally during penetration of an anatomical cavity wall and are biased to move distally upon entering the anatomical cavity. By "penetrating components" is meant those elements of the safety penetrating instrument that enter an anatomical cavity, such as the portal sleeve, safety shield and penetrating member of the safety penetrating instrument; and retraction of the penetrating member to a position where the distal end of the penetrating member is protected can be conditioned upon distally-biased movement of one or more of the penetrating components, such as the portal sleeve, the safety shield and/or the penetrating member, depending on the type and number of locking and releasing mechanisms provided. Furthermore, distal ends of the portal sleeve, the safety shield and/or the penetrating member can be aligned prior to penetration to define a smooth distal profile for penetrating anatomical tissue and can be substantially maintained in alignment during penetration by permitting proximal movement of the penetrating member, portal sleeve and/or safety shield. Alternatively, the distal ends of the portal sleeve and/or the safety shield can be distally or proximally spaced from the penetrating member distal end such that movement of the portal sleeve, safety shield and/or penetrating member in response to tissue contact will cause the distal ends of the portal sleeve, safety shield and penetrating member to become aligned. If the portal sleeve and/or safety shield distal ends are distally spaced from the penetrating member distal end in the extended rest position, the portal sleeve and/or safety shield will also function as safety members to protect the penetrating member distal end even in the event that the penetrating member is not retracted.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal end of the portal sleeve can be chamfered or blunt, smooth or roughened, or have any other configuration depending on the need for ease of penetration or increased resistance. The strength of the bias members biasing the portal sleeve, safety shield and/or penetrating member can be chosen according to differences in the resistant forces acting on the portal sleeve, safety shield and penetrating member in order to maintain a smooth distal profile during penetration.

Figure 14:
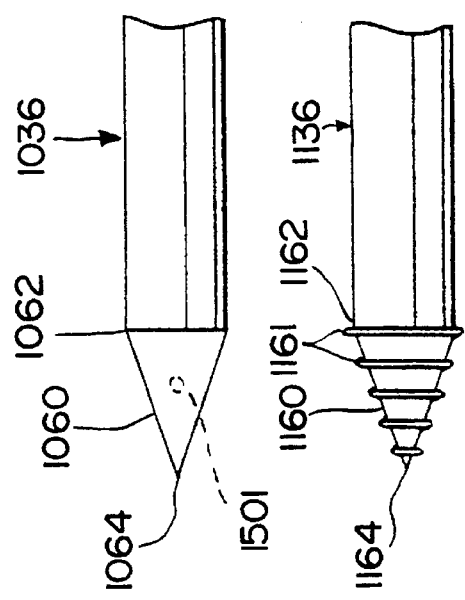
FIGS. 14–18 are fragmentary side views of alternative distal configurations for the penetrating member of the safety penetrating instrument of the present invention.
Figure 15:
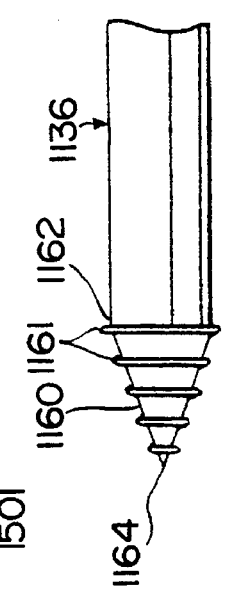
Figure 16:
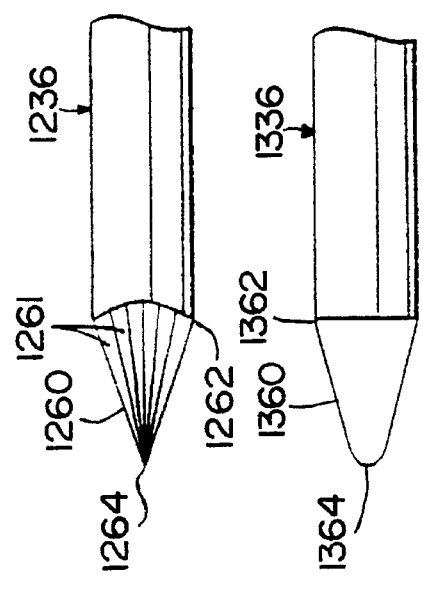
Figure 17:
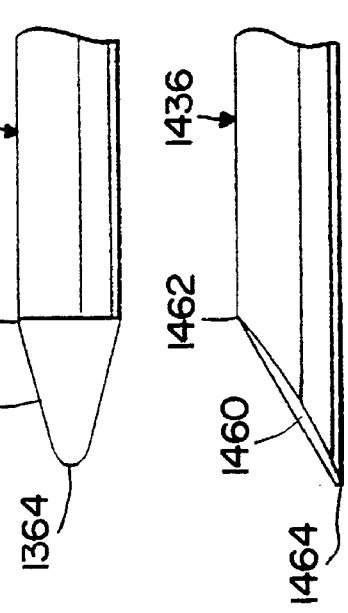
Figure 18:
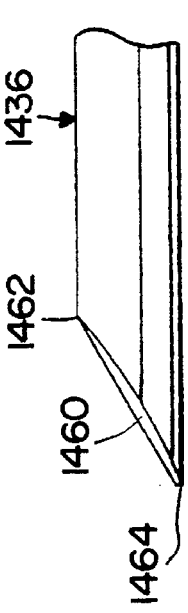

The distal end of the penetrating member can have any configuration desired for a particular procedure, for example, the pyramidal trocar configuration shown or a conical distal end 1060 tapering from a junction 1062 to a tip 1064 as shown in FIG. 14, a screw-type distal end 1160 having helical threads 1161 as shown in FIG. 15, a multi-faceted distal end 1260 having two or more facets 1261 as shown in FIG. 16, a blunt distal end 1360 with a generally conical portion terminating in a rounded or flattened tip 1364 as shown in FIG. 17, or a beveled distal end 1460 as shown in FIG. 18. Additionally, the surface defining the distal end of the penetrating member can be irregular or smooth, continuous or disjointed, provided with cutting features or having any combination of the above. Any of the penetrating members shown and described herein can include a viewing port, like the viewing port shown in phantom at 1501 in FIG. 14, for accommodating conventional optical viewing systems such as those utilizing fiber optics so that tissue can be visualized during penetration.

The rail member can have various configurations to engage the latch and be released by the trigger. Preferably, the rail member will have a configuration to serve as a stop or abutment for the penetrating member as exemplified herein by a U-shaped rail member.

The locking and releasing mechanisms require only a latch for locking the penetrating member in the extended position and a trigger for releasing the latch in response to distal movement of an operating member such as a flange carried by the penetrating member, safety shield and/or portal sleeve; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in U.S. Pat. Nos. 5,330,432; 5,324, 268; 5,320,610; 5,336,176; and 5,360,405 to Yoon and Applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196, 027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and pending applications listed above also disclose various bias arrangements useful with the safety penetrating instrument of the present invention. Other locking and releasing mechanisms that can be used in the safety penetrating instrument of the present invention are disclosed in Applicant's pending applications Ser. Nos. 08/279,170 and 08/279,172, filed Jul. 22, 1994, the disclosures of which are incorporated herein by reference.

When a latch arm, such as latch arm 465, is disposed within a hollow portion of a penetrating member for engaging the penetrating member, the latch arm can be pivotally mounted at a proximal end to the hub as shown or mounted within the penetrating member or a guide tube for pivotal movement about a center of the arm or about any other portion of the arm. In addition, such a latch arm can be embodied in a spring strip held in compression within the penetrating member or a guide tube and configured to form or carry latching and triggering protrusions. Furthermore, when latch arms are disposed within the penetrating member or a guide tube, operating members can be carried by the penetrating member, safety shield and/or portal sleeve on inside surfaces thereof for engaging triggering portions of the latch arms within the penetrating members to release latching portions of the latch arms holding the penetrating members in their extended positions. Latch arms having such features are shown and described in applicant's pending applications Ser. Nos. 08/279,170 and 08/279,172, filed Jul. 22, 1994.

One or more control buttons, such as the control buttons described in Applicant's copending patent application, Ser. No. 08/083,220, filed Jun. 24, 1993, can be mounted next to any latch for manually disengaging the latch to prevent locking of the penetrating member in the extended position. Furthermore, additional latches can be provided or existing latches modified to carry pawls or form latching surfaces for locking a penetrating member in the retracted position and can then be released through the use of a control button as described above to permit the penetrating member to be moved distally to the locked extended position prior to use.

It will also be appreciated that after penetration of the safety penetrating instrument into the anatomical cavity, the distally-biased portal sleeve and/or safety shield can act as a shock absorber upon inadvertent contact with tissue. The distal bias for the triggering member (i.e., the portal sleeve, safety shield and/or penetrating member) of the safety penetrating instrument need only be strong enough to allow slight movement of the member during penetration such that the force-to-penetrate can be minimized.

The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate portal sleeve having a proximal end fixedly secured to said housing and a distal end for introduction in the anatomical cavity;

a penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;

a safety shield disposed between said portal sleeve and said penetrating member, said safety shield being movable relative to said portal sleeve between an extended safety shield rest position protecting said penetrating member distal end when said penetrating member is retracted and a safety shield retracted position exposing said penetrating member distal end when said penetrating member is extended;

safety shield bias means for biasing said safety shield distally toward said safety shield rest position;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position while permitting a predetermined amount of proximal movement of said penetrating member during penetration of the anatomical cavity wall;

penetrating member bias means for biasing said penetrating member distally in said locked penetrating member extended position to permit said penetrating member to move proximally during penetration of the anatomical cavity wall and distally upon introduction into the anatomical cavity; and releasing means responsive to penetration of said safety penetrating instrument into the anatomical cavity for triggering release of said locking means to permit said retracting means to move said penetrating member to said penetrating member retracted position.

2. A safety penetrating instrument as recited in claim 1 wherein said releasing means is responsive to distally-biased movement of said penetrating member upon penetrating into the anatomical cavity.

3. A safety penetrating instrument as recited in claim 1 wherein said releasing means is responsive to distally-biased movement of said safety shield upon penetrating into the anatomical cavity.

4. A safety penetrating instrument as recited in claim 3 and further comprising a rail member mounting a proximal end of said penetrating member, wherein said proximal end of said penetrating member includes a flange movable within said rail member and said locking and releasing mechanism includes a latch spring engaging said rail member to lock said penetrating member in said extended position and a trigger responsive to distally-biased movement of said penetrating member flange for releasing said latch spring.

5. A safety penetrating instrument as recited in claim 1 wherein said releasing means is responsive to distally-biased movement of said portal sleeve and said penetrating member upon penetrating into the anatomical cavity.

6. A safety penetrating instrument as recited in claim 5 and further comprising a hub and a rail member movably disposed within said hub for mounting a proximal end of said penetrating member, wherein said proximal end of said penetrating member includes a flange movable within said rail member and said locking and releasing mechanism includes a latch spring disposed within said hub for engaging said rail member to lock said penetrating member in said extended position and a trigger responsive to distally-biased movement of said penetrating member flange for releasing said latch spring; and wherein at least a portion of said penetrating member is hollow and said locking and releasing means further includes a latch arm extending through said hollow portion of said penetrating member and carrying a proximal latching protrusion for engaging said rail member to lock said penetrating member in said extended position and a distal triggering protrusion for being engaged by an operating member carried by said portal sleeve to release said latching protrusion from said rail member, wherein said operating member includes a lever pivotally mounted within said housing to engage said triggering protrusion and to be engaged by an arm extending proximally from said portal sleeve.

7. A safety penetrating instrument as recited in claim 1 wherein said penetrating member distal end extends distally from a junction where a transverse dimension of said penetrating member changes and wherein said safety shield distal end is aligned with said junction when said safety shield is in said rest position and said penetrating member is in said locked penetrating member extended position.

8. A safety penetrating instrument as recited in claim 1 wherein said penetrating member distal end extends distally from a junction where a transverse dimension of said penetrating member changes and wherein said safety shield distal end is located proximally of said junction when said safety shield is in said rest position and said penetrating member is in said locked penetrating member extended position.

9. A safety penetrating instrument as recited in claim 1 wherein said penetrating member distal end extends distally from a junction where a transverse dimension of said penetrating member changes and wherein said safety shield distal end is located distally of said junction when said safety shield is in said rest position and said penetrating member is in said locked penetrating member extended position.

10. A safety penetrating instrument for establishing a portal in the wall of an anatomical cavity comprising a housing;

an elongate portal sleeve having a proximal end mounted by said housing and a distal end for introduction in the anatomical cavity, said portal sleeve being movable relative to said housing between an extended rest position and a proximally spaced retracted position;

portal sleeve bias means for biasing said portal sleeve distally toward said portal sleeve rest position;

a penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;

a safety shield disposed between said portal sleeve and said penetrating member, said safety shield being movable relative to said penetrating member between an extended safety shield rest position protecting said penetrating member distal end when said penetrating member is retracted and a safety shield retracted position exposing said penetrating member distal end when said penetrating member is extended;

safety shield bias means for biasing said safety shield distally toward said safety shield rest position;

retracting means for moving said penetrating member from said penetrating member extended position to said penetrating member retracted position;

means for manually moving said penetrating member from said penetrating member retracted position to said penetrating member extended position;

locking means for locking said penetrating member in said penetrating member extended position and preventing proximal movement of said penetrating member during penetration of the anatomical cavity wall; and releasing means responsive to penetration of said safety penetrating instrument into the anatomical cavity for triggering release of said locking means to permit said retracting means to move said penetrating member proximally to said penetrating member retracted position.

11. A safety penetrating instrument as recited in claim 10 wherein said releasing means is responsive to distally-biased movement of said portal sleeve upon penetrating into the anatomical cavity.

12. A safety penetrating instrument as recited in claim 11 wherein at least a portion of said penetrating member is hollow and wherein said locking and releasing means includes a latch arm extending through said hollow portion of said penetrating member and carrying a proximal latching protrusion for engaging said penetrating member to lock said penetrating member in said extended position and a distal triggering protrusion for being engaged by an operating member carried by said portal sleeve to release said latching protrusion from said penetrating member.

13. A safety penetrating instrument as recited in claim 12 wherein said operating member includes a lever pivotally mounted within said housing to engage said triggering protrusion and to be engaged by an arm extending proximally from said portal sleeve.

14. A safety penetrating instrument as recited in claim 10 wherein said releasing means is responsive to distally-biased movement of said safety shield upon penetrating into the anatomical cavity.

15. A safety penetrating instrument as recited in claim 10 wherein said releasing means is responsive to distally-biased movement of said portal sleeve and said safety shield upon penetrating into the anatomical cavity.

16. A safety penetrating instrument as recited in claim 10 wherein said penetrating member distal end extends distally from a junction where a transverse dimension of said penetrating member changes and wherein said safety shield distal end is aligned with said junction when said safety shield is in said rest position and said penetrating member is in said locked penetrating member extended position.

17. A safety penetrating instrument as recited in claim 10 wherein said penetrating member distal end extends distally from a junction where a transverse dimension of said penetrating member changes and wherein said safety shield distal end is located proximally of said junction when said safety shield is in said rest position and said penetrating member is in said locked penetrating member extended position.

18. A safety penetrating instrument as recited in claim 10 wherein said penetrating member distal end extends distally from a junction where a transverse dimension of said penetrating member changes and wherein said safety shield distal end is located distally of said junction when said safety shield is in said rest position and said penetrating member is in said locked penetrating member extended position.

19. A safety penetrating instrument for establishing a portal in the wall of an anatomical cavity comprising
   a housing;
   an elongate portal sleeve having a proximal end mounted by said housing and a distal end for introduction in the anatomical cavity, said portal sleeve being movable relative to said housing between an extended rest position and a proximally spaced retracted position;
   portal sleeve bias means for biasing said portal sleeve distally toward said portal sleeve rest position;
   a penetrating member disposed within said portal sleeve and having a distal end for penetrating the anatomical cavity wall, said penetrating member being movable relative to said portal sleeve between an extended position where said distal end of said penetrating member protrudes distally from said distal end of said portal sleeve and a retracted position proximally spaced from said extended position;
   a safety shield disposed between said portal sleeve and said penetrating member, said safety shield being movable relative to said penetrating member between an extended safety shield rest position protecting said penetrating member distal end when said penetrating member is retracted and a safety shield retracted position exposing said penetrating member distal end when said penetrating member is extended;
   safety shield bias means for biasing said safety shield distally toward said safety shield rest position;
   retracting means for moving said penetrating member from said penetrating member extended position to said penetrating member retracted position;
   means for manually moving said penetrating member from said penetrating member retracted position to said penetrating member extended position;
   locking means for locking said penetrating member in said penetrating member extended position while permitting a predetermined amount of proximal movement of said penetrating member during penetration of the anatomical cavity wall;
   penetrating member bias means for biasing said penetrating member distally in said locked penetrating member extended position to permit said penetrating member to move proximally during penetration of the anatomical cavity wall and distally upon introduction into the anatomical cavity; and
   releasing means responsive to penetration of said safety penetrating instrument into the anatomical cavity for triggering release of said locking means to permit said retracting means to move said penetrating member proximally to said penetrating member retracted position.

20. A safety penetrating instrument as recited in claim 19 wherein said releasing means is responsive to distally-biased movement of said penetrating member upon penetrating into the anatomical cavity.

21. A safety penetrating instrument as recited in claim 19 wherein said releasing means is responsive to distally-biased movement of said safety shield upon penetrating into the anatomical cavity.

22. A safety penetrating instrument as recited in claim 19 wherein said releasing means is responsive to distally-biased movement of said portal sleeve upon penetrating into the anatomical cavity.

23. A safety penetrating instrument as recited in claim 22 wherein at least a portion of said penetrating member is hollow and wherein said locking and releasing means includes a latch arm extending through said hollow portion of said penetrating member and carrying a proximal latching protrusion for engaging said penetrating member to lock said penetrating member in said extended position and a distal triggering protrusion for being engaged by an operating member carried by said portal sleeve to release said latching protrusion from said penetrating member.

24. A safety penetrating instrument as recited in claim 23 wherein said operating member includes a lever pivotally mounted within said housing to engage said triggering protrusion and to be engaged by an arm extending proximally from said portal sleeve.

25. A safety penetrating instrument as recited in claim 19 wherein said penetrating member distal end extends distally from a junction where a transverse dimension of said penetrating member changes and wherein said safety shield distal end is aligned with said junction when said safety shield is in said rest position and said penetrating member is in said locked penetrating member extended position.

26. A safety penetrating instrument as recited in claim 19 wherein said penetrating member distal end extends distally from a junction where a transverse dimension of said penetrating member changes and wherein said safety shield distal end is located proximally of said junction when said safety shield is in said rest position and said penetrating member is in said locked penetrating member extended position.

27. A safety penetrating instrument as recited in claim 19 wherein said penetrating member distal end extends distally from a junction where a transverse dimension of said penetrating member changes and wherein said safety shield distal end is located distally of said junction when said safety shield is in said rest position and said penetrating member is in said locked penetrating member extended position.

28. A safety penetrating instrument as recited in claim 19 wherein said releasing means is responsive to distally-biased movement of said portal sleeve and said penetrating member upon penetrating into the anatomical cavity.

29. A safety penetrating instrument as recited in claim 19 wherein said releasing means is responsive to distally-biased movement of said safety shield and said penetrating member upon penetrating into the anatomical cavity.

* * * * *